United States Patent [19]

Lecomte et al.

[11] Patent Number: 4,758,725
[45] Date of Patent: Jul. 19, 1988

[54] CALIBRATION DEVICE FOR NUCLEAR MEDICINE EQUIPMENT AND IT USE PROCESS

[75] Inventors: Jean-Luc Lecomte, Echirolles; Michel Martin, Eybens; Francis Sauvage, Moirans; Edmond Tournier, Grenoble, all of France

[73] Assignee: Commissariat a l'Energie Atomique, Paris, France

[21] Appl. No.: 921,131

[22] Filed: Oct. 21, 1986

[30] Foreign Application Priority Data

Oct. 25, 1985 [FR] France ................................ 85 15887

[51] Int. Cl.⁴ ............................................ G01T 1/164
[52] U.S. Cl. .............................. 250/363 R; 250/252.1
[58] Field of Search ............ 250/252.1, 363 SG, 428, 250/433, 507.1, 506.1, 496.1, 497.1, 432 R, 435; 378/206, 18, 159, 207

[56] References Cited

U.S. PATENT DOCUMENTS

| | | | |
|---|---|---|---|
| 3,917,124 | 4/1975 | Kifer | 222/386 |
| 4,446,570 | 5/1984 | Guth | 250/505.1 |
| 4,527,057 | 7/1985 | Guyton et al. | 250/252.1 |

FOREIGN PATENT DOCUMENTS 2535182  2/1977  Fed. Rep. of Germany .

OTHER PUBLICATIONS

K. J. Murray, "A New Phantom for the Assessment of Nuclear Medicine Imaginig Equipment", Jan., 1979, 188-192.

*Primary Examiner*—Carolyn E. Fields
*Assistant Examiner*—John A. Miller
*Attorney, Agent, or Firm*—Oblon, Fisher, Spivak, McClelland & Maier

[57] ABSTRACT

This device comprises a liquid radioactive source which, when the patient is absent, is used for calibrating the ionizing radiation detectors of the apparatus and is located in a container which can contains the source. The device comprises a storage magazine communicating with the container by at least one pipe and means for transferring the liquid source from the storage magazine to the container and vice-versa, the container being fixed with respect to the apparatus and the magazine having a volume at least equal to that of the container.

13 Claims, 3 Drawing Sheets

CALIBRATION DEVICE FOR NUCLEAR MEDICINE EQUIPMENT AND IT USE PROCESS

FIELD OF THE INVENTION

The present invention relates to a calibration device for nuclear medicine equipment and to its use process. The invention applies to the calibration of ionizing radiation detectors used in nuclear medicine equipment for observing a patient who has previously been made radioactive. These nuclear medicine equipment are, e.g., position tomographs, gamma cameras, and gamma tomographs.

BACKGROUND OF THE INVENTION

In known manner, for calibrating ionizing radiation detectors of a nuclear medicine apparatus, use is made of a liquid radioactive source maintained in a container. This container is placed in the detection zone of the detectors prior to each observation of a patient.

FIG. 1 diagrammatically shows a nuclear medicine apparatus 2, within which is placed a known type of container 6, containing a liquid radioactive source 1. The apparatus 2 comprises a group of detectors 4 e.g., placed in the case of a tomography apparatus in such a way as to form a cylinder or a portion of a cylinder. The inner zone of the cylinder corresponds to the detection zone 8 of the apparatus 2.

The group of detectors 4 is generally mobile, so that it is possible to observe the patient in all directions in space, when he is placed in the centre of the detection zone 8.

The container 6 has a shape adapted to the group of detectors 4. It is therefore cylindrical in the case of a tomography apparatus, and its length generally exceeds that of the latter.

As shown in FIG. 1, the container 6 is formed by an annular chamber containing the liquid radioactive source 1, or by a winding of turns filled with the source 1.

During a calibration operation, the container 6 is placed in the detection zone 8 so that it is centered with respect to the group of detectors 4.

Following each calibration, the container 6 is removed from the detection zone 8, so as not to disturb the measurements performed on a patient placed in the centre of the detection zone. The container 6 is then placed in a shielded enclosure 10, which is generally made from lead in order to protect the environment from ionizing radiation emitted by the source 1 in the container 6.

In known manner, the container 6 is alternately placed in the detection zone 8 and in the enclosure 10, either manually by an operator or by automatically controlled displacement means (not shown).

The manual method of introducing the container 6 into the detection zone 8 and its arrangement in the enclosure 10 makes it possible not to overburden the detection zone with control means. However, this method does not protect personnel from ionizing radiation.

The automatic control method makes it necessary to at least partly place the enclosure 10 in the detection zone 8. Automatic displacement controls then make it possible to place the container 6 either in the centre of the detection zone 8, or in the enclosure 10. Thus, this method makes it possible to avoid exposure of personnel, but makes it necessary to place the automatic displacement control means and the enclosure at least partly in the detection zone, which greatly overburdens the latter.

OBJECT OF THE INVENTION

The object of the present invention is to obviate the aforementioned disadvantages.

SUMMARY OF THE INVENTION

The subject invention provides a calibration device comprising a container which is fixed with respect to the detection zone of a nuclear medicine apparatus.

The container contains the liquid radioactive source only during the calibration operations of the apparatus. The device according to the invention simultaneously makes it possible not to expose personnel to ionizing radiation and not to overburden the detection zone with control means.

More specifically, the present invention relates to a calibration device for a nuclear medicine apparatus used for observing a patient who has previously been made radioactive, comprising a liquid radioactive source used for the calibration of the ionizing radiation detectors of the apparatus and located in a container which can contain the source. The device comprises a storage magazine communicating with the container by at least one pipe and means for transferring the liquid radioactive source from the storage magazine to the container and vice-versa, the container being fixed with respect to the apparatus and the storage magazine having a volume at least equal to that of the container.

The storage magazine is located in a zone ensuring that the detection zone is not overburdened. The magazine comprises means for stopping the ionizing radiation constituted either by the very walls of the magazine, or by protection means such as lead plates surrounding the magazine. However, the container is made from a material permitting the passage of such radiation, such as stainless steel or aluminum.

According to a preferred embodiment of the calibration device, the means for transferring the liquid radioactive source comprise a flat tight elastic diaphragm disposed in the container so as to produce therein first and second chambers with variable volumes, the first chamber being connected to the storage magazine and the second chamber being connected to first means for introducing and discharging pressurized gases.

According to another preferred embodiment of the calibration device, the means for transferring the liquid source comprise a second tight elastic diaphragm disposed in the storage magazine so as to form therein first and second enclosures with variable volumes, the first enclosure being connected to the container and the second enclosure being connected to second means for the introduction and removal of pressurized gases.

Advantageously, the container is toric, the first diaphragm is conical, and the first and second chambers are toric, one of the chambers surrounding the other. In this case, the container shape is adapted to that of a group of detectors arranged in accordance with a cylinder, as in the case of a tomograph.

The term "toric" when related to the container shape and that of the first and second chambers means an annular shape, whereof the cross-section is of random form.

Preferably, the first and second enclosures are respectively shaped like a saucer and are joined along their larger section by the second diaphragm.

According to another embodiment of the calibration device, the first means for introducing and removing gases comprise a reserve pressurized gas balloon connected by a pipe to the second chamber.

According to another embodiment of the calibration device, the second gas introduction and removal means comprise gas introduction means having gas storage means connected to the second enclosure by a first pipe having first opening and closing means and gas removal means involving placing the second enclosure under ambient air conditions, those means having second opening and closing means.

Advantageously these gas removal means involving placing the second enclosure under ambient air conditions comprise a vessel connected to the first pipe by a second pipe, the vessel also being connected to a third pipe which is open to the ambient air, the second pipe having second opening and closing means and pressure limiting means.

According to another embodiment, the calibration device comprises means for removing air from the first enclosure and the first chamber. These means are advantageously connected to the first enclosure, the storage magazine generally being positioned above the container. However, they can also be connected to the first chamber.

According to another embodiment, the calibration device comprises means for introducing and removing the liquid radioactive source, particularly for the replacement thereof. These means are preferably connected to the first chamber, the container generally being positioned below the storage magazine. However, they can also be connected to the first chamber.

The invention also relates to a process for using the calibration device, wherein the liquid radioactive source is in the first enclosure, so that the liquid source is transferred into the first chamber by introducing pressurized gas into the second enclosure by the second pressurized gas introduction and removal means.

According to another embodiment of the process, the liquid radioactive source is in the first chamber, so that the liquid radioactive source is transferred into the first enclosure by discharging the gas from the second enclosure by the second pressurized gas introduction and removal means.

BRIEF DESCRIPTION OF THE DRAWINGS

The invention is described in greater detail hereinafter relative to non-limitative embodiments and with reference to the attached FIGS. 2 to 4, wherein.

DETAILED DESCRIPTION OF THE PREFERRED EMBODIMENTS

Figure 1:
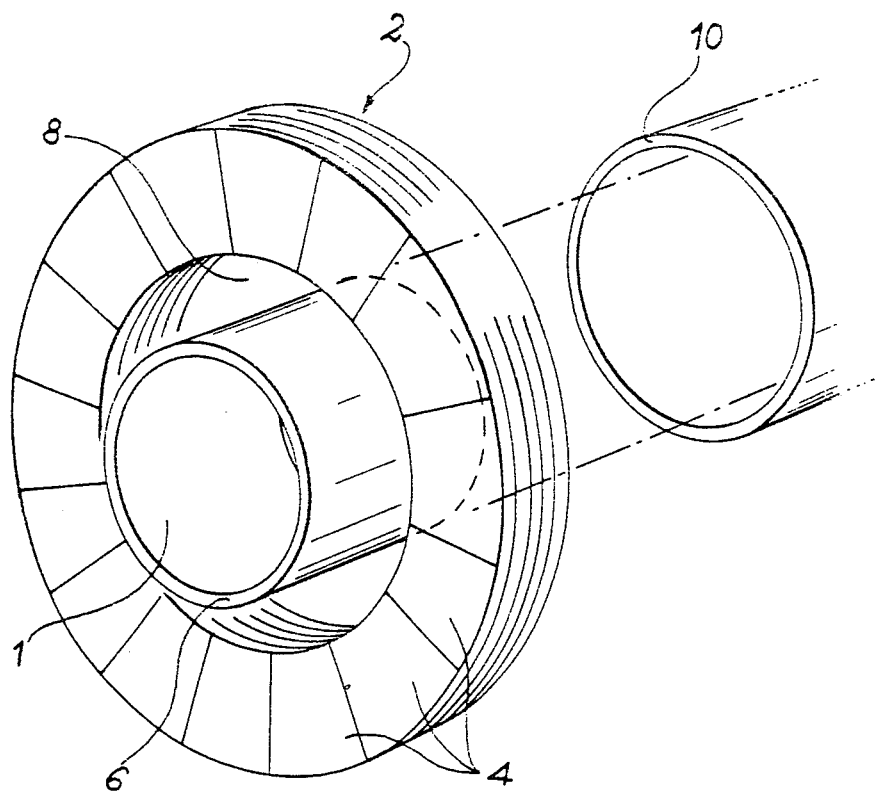
Figure 2:
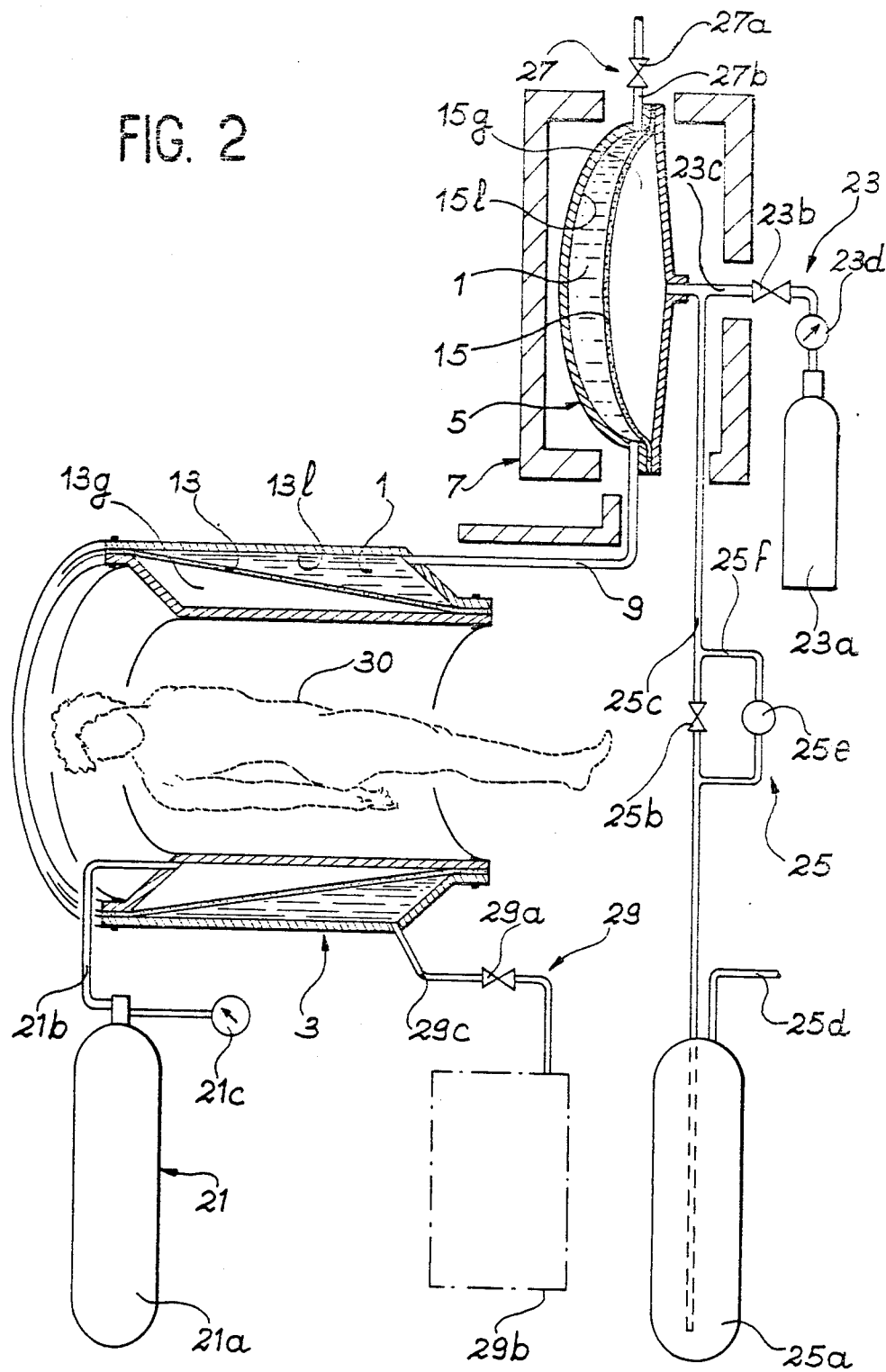
FIG. 2, diagrammatically shows an embodiment of a calibration device according to the invention.

FIG. 2 shows an embodiment of a calibration device according to the invention—e.g., for a positon tomograph. This device comprises a container 3 connected by a pipe 9 to a storage magazine 5 and a liquid radioactive source 1, which can be transferred from the storage magazine 5 to the container 3 and vice-versa by transfer means.

These transfer means comprise a first tight elastic diaphragm 13 located in the container 3 so as to form therein a first chamber 131 which can receive the liquid radioactive source 1 and a second chamber 13g which can receive pressurized gas.

The transfer means also comprise a second tight elastic diaphragm 15 located in the storage magazine 5 so as to produce a first enclosure 15l able to receive the liquid radioactive source 1 and a second enclosure 15g able to receive the pressurized gas.

The first chamber 131 and the first enclosure 151 are interconnected by the pipe 9. Moreover, the second chamber 13g is connected to pressurized gas introduction and removal means 21, and the second enclosure 15g is connected to pressurized gas introduction and removal means 23, 25. The height of the storage magazine 5 generally exceeds that of the container 3. Moreover, for the discharge of the gas present in the first chamber 13l and the first enclosure 15l, gas discharge means 27 are preferably connected to the first enclosure 15l at the highest level thereof. The gas discharge means 27 may, e.g., comprise a pipe 27b connected to the first enclosure 15l and to the atmosphere, the pipe 27b having opening and closing means, such as a valve 27a.

Moreover, for introducing the liquid radioactive source 1 into the device according to the invention and for removing the liquid radioactive source 1, particularly in the case of the second diaphragm 15 rupturing or for replenishing or replacing the liquid radioactive source 1, means 29 for introducing and removing the source are preferably connected to the first chamber 131 at its lowest level.

The means 29, may, e.g., comprise a pipe 29c connected on the one hand to the first chamber 13l and on the other to means 29b for receiving the liquid radioactive source 1 or containing the the liquid radioactive source 1 to be introduced, the pipe 29c having opening and closing means, such as a valve 29a.

The detectors used in a tomograph are distributed in accordance with a cylinder or a cylinder portion. Thus, in the particular case of a tomograph, the container 3 is in the form of a cylinder having a smaller diameter than a cylinder formed by the group of detectors, but the length of which slightly exceeds that of the group. The container 3 is centered in the detection zone formed by the detectors and is fixed with respect thereto.

Moreover, in the case of a cylindrical toric container, the first elastic diaphragm 13 is conical, and the two chambers 13l and 13g are toric, the first chamber 13l preferably surrounding the second chamber 13g.

The container 3 is made from an ionizing radiation-transparent material, the material being, for example, aluminium.

The two enclosures 15l, 15g of the storage magazine 5 are, e.g., constituted by two sources joined along their largest section by the second elastic diaphragm 15. The storage magazine 5 comprises means for stopping ionizing radiation constituted by the walls of the storage magazine 5 or by protective means, such as lead plates 7 surrounding the storage magazine 5. This also applies to the pipe 9.

The pressurized gas introduction and removal means 21 may, e.g., comprise a balloon 21a containing the pressurized gas and connected to the second chamber 13g by a pipe 21b. The balloon 21a is open to the second chamber 13g.

Moreover, a pressure gauge 21c can be connected to the gas balloon 21a in order to monitor the different transfers of the liquid radioactive source 1 or the possible rupturing of the first diaphragm 13.

The pressurized gas introduction and removal means 23, 25 are subdivided into gas introduction means 23 and gas removal means 25. The gas introduction means 23, e.g., have gas storage means, such a reservoir 23a connected to the second enclosure 15g by a pipe 23c. The pipe 23c has a gas expansion means 23d and opening and closing means, such as an electrovalve 23b. The gas removal means 25 may, e.g., incorporate a vessel 25a connected to the second enclosure 15g via a pipe 25c connected to the pipe 23c. The vessel 25a is also connected to a pipe 25d open to the ambient air. The pipe 25c comprises opening and closing means, such as an electrovalve 25b and a pressure limiter, such as a calibrated spring 25e placed in a pipe 25f parallel to the electrovalve 25b. The ends of the pipe 25f are connected to the pipe 25c. The vessel 25a makes it possible to collect the liquid radioactive source 1 if the second diaphragm 15 ruptures.

A patient 30 is placed in the centre of the container 3 to be examined only when the container 3 no longer contains the liquid radioactive source 1.

The remainder of the description provides a better understanding of the operation of the calibration device according to the invention.

When the electrovalve 23b is closed and the electrovalve 25b open, the second enclosure 15g is at atmospheric pressure. The liquid radioactive source 1 contained in the first chamber 13l is transferred to the first enclosure 15l under the action of the pressurized gas from the balloon 21a, which forces the first diaphragm 13 against the wall of the first chamber 13l. This gas expands in the second chamber 13g, which increases the volume, whereas the volume of the first chamber 13l decreases. Moreover, the second diaphragm 15 is forced against the wall of the second enclosure 15g by the liquid radioactive source 1. Thus, the volume of the second enclosure 15g decreases and the voume of the first enclosure 15l increases.

Figure 3:
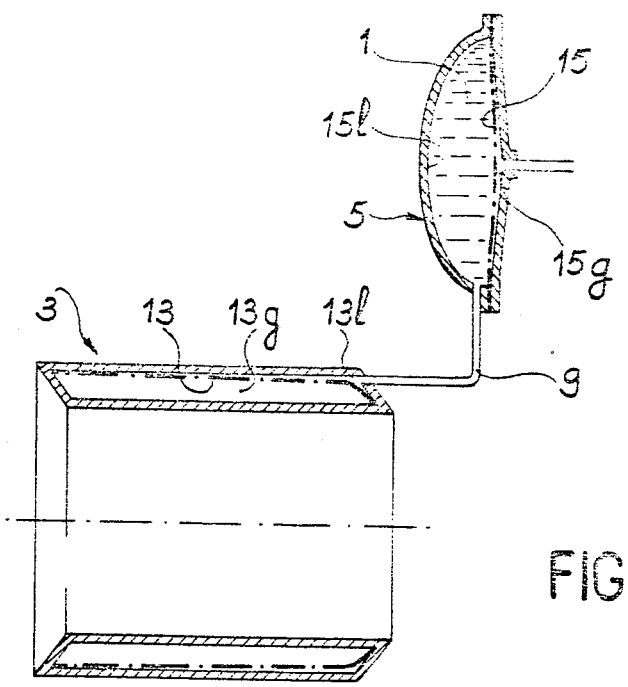
FIG. 3, diagrammatically shows the container and storage magazine of the device of FIG. 2 respectively containing pressurized gas and the liquid radioactive source.

As shown in FIG. 3, when all of the liquid radioactive source 1 has been transferred to the first enclosure 15l, the volume of the latter and of the second chamber 13g are at a maximum and tend to be respectively equal to the total volume of the storage magazine 5 and the total volume of the container 3. The volumes of the second enclosure 15g and the first chamber 13l are consequently substantially zero.

To transfer the liquid radioactive source 1 from the first enclosure 15l to the first chamber 131, the electrovalve 25b is closed and the electrovalve 23b opened. Gas contained in the reservoir 23a, expanded by the gas expansion means 23d, enters the second enclosure 15g via the pipe 23c. This gas forces the second diaphragm 15 against the wall of the first enclosure 15l. Thus, the liquid radioactive source 1 is removed from the first enclosure 15l and passed into the first chamber 13l. Therefore the first diaphragm 13 is forced against the wall of the second chamber 13g, and the gas which was previously in the second chamber 13g is now compressed in the balloon 21a.

Figure 4:
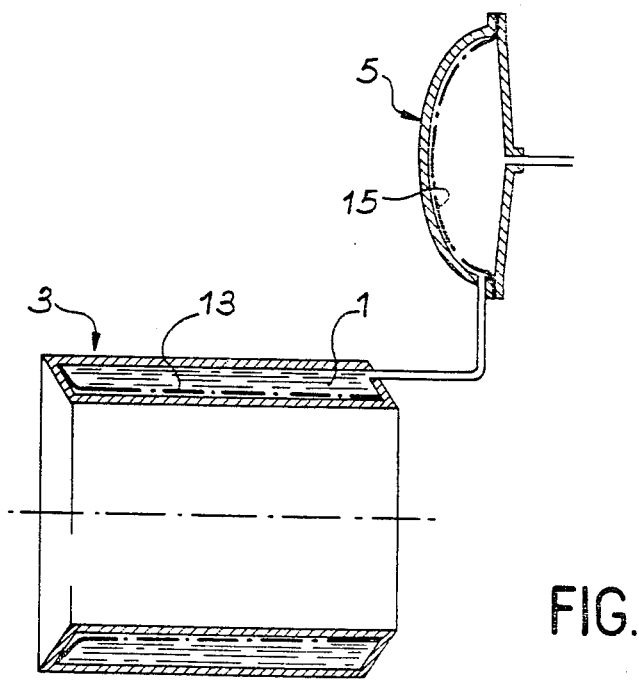
FIG. 4, diagrammatically shows the container and storage magazine of the device of FIG. 2 respectively containing the liquid radioactive source and the pressurized gas.

When all of the liquid radioactive source 1 is contained in the first chamber 13l, as shown in FIG. 4, the volume of the first chamber of 13l and the volume of the second enclosure 15g are at a maximum and are respectively equivalent to the total volume of the container 3 and to the total volume of the storage magazine 5. The volumes of the second chamber 13g and the first enclosure 15l are then substantially zero.

FIG. 2 shows an intermediate phase with respect to those shown in FIGS. 3 and 4. This intermediate phase corresponds to a transfer phase of the liquid radioactive source 1 from the first chamber 13l to the first enclosure 15l or vice-versa.

The use of elastic diaphragms in the device according to the invention obviates the problem of gas bubbles inherent in liquid radioactive sources. This homogeneity of the liquid radioactive source 1 is also due to the shape of the container 3 and the presence of the first diaphragm 13. Furthermore, no supplementary movement of the liquid radioactive source 1 is necessary to obviate the problem of such inhomogeneities.

Moreover, the elastic diaphragms 13, 15 the shape of the container 3, and the shape of the storage magazine 5 make it possible to respectively obtain a minimum residual volume in both the container 3 and the storage magazine 5. The minimum residual volumes make it possible to transfer all the liquid radioactive source 1 from the first chamber 13l to the first enclosure 15l or vice-versa. A residual volume corresponds to the volume remaining between a wall of the container 3 or the storage magazine 5 and the corresponding diaphragm when the latter is forced against the wall.

The embodiment described hereinbefore is non-limitative, and other container and magazine forms can be envisaged without passing beyond the scope of the invention. The shape of the container more particularly varies as a function of the nuclear medecine apparatus for which it is used, its shape adapting to the detection zone of such apparatus.

What is claimed is:

1. A calibrating device for a nuclear medicine apparatus comprising means for observing a patient who has previously been made radioactive and at least one ionizing radiation detector, said calibrating device comprising:
    (a) a radioactive liquid used for the calibration of said at least one ionizing radiation detector;
    (b) a container;
    (c) a storage magazine communicating with said container by at least one pipe and having a volume at least equal to the volume of said container; and
    (d) means for transferring said radioactive liquid from said storage magazine to said container and vice versa, said means for transferring comprising:
        (i) a tight elastic diaphragm located in said container so as to produce in said container first and second chambers with variable volumes, said first chamber being connected to said storage magazine, and
        (ii) pressurized gas introduction and removal means connected to said second chamber.

2. A calibrating device according to claims 1, wherein said means for transferring further comprises:
    (a) a tight elastic diaphragm located in said storage magazine so as to produce in said storage magazine first and second enclosures with variable volumes, said first enclosure being connected to said container, and
    (b) pressurized gas introduction and removal means connected to said second enclosure.

3. A calibrating device according to claim 1, wherein:
(a) said container is toric;
(b) said tight elastic diaphragm is conical; and
(c) said first and second chambers are toric, one of said first and second chambers surrounding the other.

4. A calibrating device according to claim 1, wherein said pressurized gas introduction and removal means connected to said second chamber comprise a pressurized gas balloon connected by a pipe to said second chamber.

5. A calibrating device for a nuclear medicine apparatus comprising means for observing a patient who has previously been made radioactive and at least one ionizing radiation detector, said calibrating device comprising:
(a) a radioactive liquid used for the calibration of said at least one ionizing radiation detector;
(b) a container;
(c) a storage magazine communicating with said container by at least one pipe and having a volume at least equal to the volume of said container; and
(d) means for transferring said radioactive liquid from said storage magazine to said container and vice versa, said means for transferring comprising:
  (i) tight elastic diaphragm located in said storage magazine so as to produce in said storage magazine first and second enclosures with variable volumes, said first enclosure being connected to said container, and
  (ii) pressurized gas introduction and removal means connected to said second enclosure.

6. A calibrating device according to claim 5, wherein:
(a) each of said first and second enclosures has a saucer shape and
(b) said first and second enclosures are joined along their largest section by said tight elastic diaphragm.

7. A calibrating device according to claim 5, wherein said pressurized gas introduction and removal means comprise:
(a) gas introduction means having means for storing gas connected to said second enclosure by a first pipe having first opening and closing means and
(b) gas removal means comprising:
  (i) means for placing said second enclosure under ambient air conditions and
  (ii) second opening and closing means.

8. A calibrating device according to claim 7, wherein said means for placing said second enclosure under ambient air conditions comprises:
(a) a vessel connected to said first pipe by a second pipe;
(b) a third pipe connecting said vessel to the ambient air; and
(c) opening and closing means and pressure limiting means contained in said second pipe.

9. A calibrating device according to claim 5 and further comprising means for discharging gas from said first enclosure, said means for discharging being connected to said first enclosure.

10. A calibrating device according to claim 5 and further comprising means for introducing and removing said radioactive liquid from said first enclosure, said means for introducing and removing being connected to said first enclosure.

11. A process for using a calibrating device for a nuclear medicine apparatus comprising means for observing a patient who has previously been made radioactive and at least one ionizing radiation detector, said calibrating device comprising:
(a) a radioactive liquid used for the calibration of said at least one ionizing radiation detector;
(b) a container;
(c) a storage magazine communicating with said container by at least one pipe and having a volume at least equal to the volume of said container; and
(d) means for transferring said radioactive liquid from said storage magazine to said container and vice versa, said means for transferring comprising:
  (i) a first tight elastic diaphragm located in said container so as to produce in said container first and second chambers with variable volumes, said first chamber being connected to said storage magazine;
  (ii) a second tight elastic diaphragm located in said storage magazine so as to produce in said storage magazine first and second enclosures with variable volume, said first enclosure being connected to said container;
  (iii) first pressurized gas introduction and removal means connected to said second chamber; and
  (iv) second pressurized gas introduction and removal means connected to said second enclosure,
said process comprising the step of transferring said radioactive liquid from said first enclosure to said first chamber by introducing pressurized gas into said second enclosure by means of said second pressurized gas introduction and removal means.

12. A process as recited in claim 11 and comprising the further step of transferring said radioactive liquid from said first chamber to said first enclosure by discharging pressurized gas from said second enclosure by means of said second pressurized gas introduction and removal means.

13. A process for using a calibrated device for a nuclear medicine apparatus comprising means for observing a patient who has previously been made radioactive and at least one ionizing radiation detector, said calibrating device comprising:
(a) a radioactive liquid used for the calibration of said at least one ionizing radiation detector;
(b) a container;
(c) a storage magazine communicating with said container by at least one pipe and having a volume at least equal to the volume of said container; and
(d) means for transferring said radioactive liquid from said storage magazine to said container and vice versa, said means for transferring comprising:
  (i) a first tight elastic diaphragm located in said container so as to produce in said container first and second chambes with variable volumes, said first chamber being connected to said storage magazine;
  (ii) a second tight elastic diaphragm located in said storage magazine so as to produce in said storage magazine first and second enclosures with variable volumes, said first enclosure being connected to said container;
  (iii) first pressurized gas introduction and removal means connected to said second chamber; and
  (iv) second pressurized gas introduction and removal means connected to said second enclosure,
said process comprising the step of transferring said radioactive liquid from said first chamber to said first enclosure by discharging pressurized gas from said second enclosure by means of said second pressurized gas introduction and removal means.

* * * * *

UNITED STATES PATENT AND TRADEMARK OFFICE
CERTIFICATE OF CORRECTION

PATENT NO. : 4,758,725

DATED : Jul. 19, 1988

INVENTOR(S) : Jean-Luc LECOMTE, et al.

It is certified that error appears in the above-identified patent and that said Letters Patent is hereby corrected as shown below:

On the Title page, and in Column 1, Line 2, the word "IT" in the Title should be --ITS--.

Signed and Sealed this

Twenty-second Day of November, 1988

Attest:

DONALD J. QUIGG

*Attesting Officer*   *Commissioner of Patents and Trademarks*